United States Patent [19]
Webb

[11] Patent Number: 5,902,234
[45] Date of Patent: May 11, 1999

[54] MEDICAL COMMUNICATION SYSTEM FOR AMBULATORY HOME-CARE PATIENTS

[76] Inventor: Nicholas J. Webb, 5370 Basel Dr., Wrightwood, Calif. 92397

[21] Appl. No.: 08/837,229

[22] Filed: Apr. 10, 1997

[51] Int. Cl.[6] .............................. G06F 15/42; A61B 5/04
[52] U.S. Cl. ............................................................ 600/300
[58] Field of Search .................................. 600/300, 301; 128/897, 898, 920–925

[56] References Cited

U.S. PATENT DOCUMENTS

| | | |
|---|---|---|
| 3,843,841 | 10/1974 | Rubinstein . |
| 4,237,344 | 12/1980 | Moore . |
| 4,284,849 | 8/1981 | Anderson et al. . |
| 4,303,801 | 12/1981 | Anderson . |
| 4,531,527 | 7/1985 | Reinhold, Jr. . |
| 4,856,047 | 8/1989 | Saunders . |
| 5,016,172 | 5/1991 | Dessertine .............................. 600/300 |
| 5,025,374 | 6/1991 | Roizen et al. ........................... 600/300 |
| 5,228,449 | 7/1993 | Christ et al. . |
| 5,390,238 | 2/1995 | Kirk et al. . |
| 5,412,372 | 5/1995 | Parkhurst ................................. 340/568 |
| 5,416,695 | 5/1995 | Stutman et al. . |
| 5,583,831 | 12/1996 | Churchill et al. .......................... 368/10 |
| 5,630,207 | 5/1997 | Gitlin et al. ............................. 455/54.1 |

*Primary Examiner*—John P. Lacyk
*Assistant Examiner*—Samuel Gilbert
*Attorney, Agent, or Firm*—David P. Gordon; David S. Jacobson; Thomas A. Gallagher

[57] ABSTRACT

A medical communication system for monitoring an ambulatory home-care patient is provided. The system includes a two-way pager worn by the patient and a computer storing the treatment plan of the patient. The computer initiates the transmission of inquiries to the pager worn by the patient and records responses transmitted by the patient back to the computerized system. The computerized system can contact the patient anywhere within a local service area. The patient responds to one or more inquiries from the system by pressing appropriate buttons on the two-way pager which are sent back to the computer. The responses are recorded by the computer. If the computer does not receive a response from the patient or if the responses do not fall within compliance guidelines, an automated phone call is initiated requesting the same information. If the patient responds to the automated phone call, the responses are recorded by the computer. If the patient fails to respond or provides non-complying responses to both the pager and the automated phone call, the treatment plan is forwarded to a staff nurse, who attempts to contact the patient by telephone. If no response or an unsatisfactory response is secured, emergency medical services and/or health care providers are contacted according to a response plan tailored to the particular patient and stored within the computer.

21 Claims, 4 Drawing Sheets

MEDICAL COMMUNICATION SYSTEM FOR AMBULATORY HOME-CARE PATIENTS

BACKGROUND OF THE INVENTION

1. Field of the Invention

This invention relates broadly to outpatient medical monitoring systems. More particularly, this invention relates to outpatient medical communication systems for ambulatory home-care patients.

2. State of the Art

Current trends within managed health care mandate reducing the costs of the delivery of health care. The most costly method of delivering health care is care within a hospital facility. Therefore, there is a prevailing trend towards discharging patients sooner in order to reduce the cost of care, and to 'treat' the patients with out-of-hospital or home-based health care. This trend toward home-based health care will continue to grow as greater cost constraints are implemented in order to manage health care at lower delivery costs.

A number of home-care systems are currently available which use basic monitoring technology. For example, U.S. Pat. No. 5,228,449 to Christ et al. discloses a one-way remote alarm system in which vital signs of a home care patient are monitored and an alarm signal is sent to a remote monitoring station in an emergency situation. U.S. Pat. No. 3,843,841 to Rubinstein discloses another health care system which automatically dials a telephone number and delivers a prerecorded message if a home residing patient fails to respond to a periodic signal. However, the above referenced systems other than generating an alarm signal in a presumed emergency situation provide no opportunity for a dialogue between the patient and the care provider. These types of systems are therefore inadequate for monitoring the general health of home care patients (i.e., reminding patients to monitor their vital signs and to self-administer medication, inquiring about medicament side-effects, monitoring the symptoms of disease, determining non-emergency care needs, and inquiring about the patient's perceived state of health) which might prevent emergency situations from occurring. In addition, systems which require a patient to remain in the vicinity of the alarm system do not meet the needs of ambulatory home-care patients.

More recently, the telemedicine trend has led to the production of more interactive devices which use costly computer screens and miniature television cameras with telephonic connections. These devices permit a greater degree of interactivity between the home-residing patient and a monitoring station than the 'emergency' alarms. However, the cost of the equipment is large, thereby limiting the use of the equipment to a selected few recipients. In addition, like more basic monitoring systems, the systems are localized, requiring the patient to be near the computer screen to interact with the system. However, a large percentage of patients that are discharged and that need to be monitored (e.g., reminded to self-administer life critical medication), are quite ambulatory.

SUMMARY OF THE INVENTION

It is therefore an object of the invention to provide systems and methods of insuring patient compliance with life critical treatment plans once the patient is released from a hospital.

It is another object of the invention to provide systems and methods of insuring patient compliance with life critical treatment which can be conveniently utilized by an ambulatory patient at or away from home.

It is a further object of the invention to provide a medical paging system which provides interactivity and a degree of multilevel inquiry.

It is an additional object of the invention to provide systems and methods of insuring patient compliance with life critical treatment which provide empirical compliance data in order to offer medical and legal verification of the responses by the patient to treatment compliance inquiries.

It is also an object of the invention to provide systems and methods of insuring patient compliance with life critical treatment which are relatively inexpensive.

In accord with these objects which will be discussed in detail below, a medical communication system for monitoring an ambulatory home-care patient is provided. The system includes a two-way pager worn by the patient and a health care provider computer system which stores the treatment plan of the patient and which is in two-way communication with the pager. The computer initiates the transmission of inquiries to the pager worn by the patient and records responses transmitted by the patient back to the computer. The system can contact the patient anywhere within a local service area, and preferably anywhere serviced by the paging system. The patient responds to one or more inquiries from the system by pressing appropriate buttons on the two-way pager which are sent back to the computer. The response is recorded by the computer. If the computer does not receive a response from the patient or if the responses do not fall within compliance guidelines, an automated phone call is initiated requesting the same information. If the patient responds to the automated phone call, the responses are recorded by the computer. If the patient fails to respond or provides at least one non-complying response to either the pager or the automated phone call, the treatment plan is forwarded to a staff nurse, who attempts to contact the patient by telephone. If no response or an unsatisfactory response is secured by the staff nurse, emergency medical services and/or health care providers are contacted according to a response plan tailored to the particular patient and stored within the patient data module stored in the computer.

It will be appreciated that the medical communication system permits an ambulatory home-care patient to be contacted within and outside the home of the patient, as the system for interacting with the patient is a portable two-way pager which can operate (i.e., receives data and sends data) over a relatively large area. Therefore, the patient is not confined to his home in order to respond to a care system stationed in his home. In addition, a multi-level inquiry is established to determine the condition of the patient and the questions of the inquiry and the responses are stored in the computer to verify and evidence that an appropriate response by the health care provider to the responses supplied by the patient has been provided. Moreover, the paging system is relatively inexpensive, especially when compared with current telemedicine systems, and provides a level of interactivity which is reassuring to the patient.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
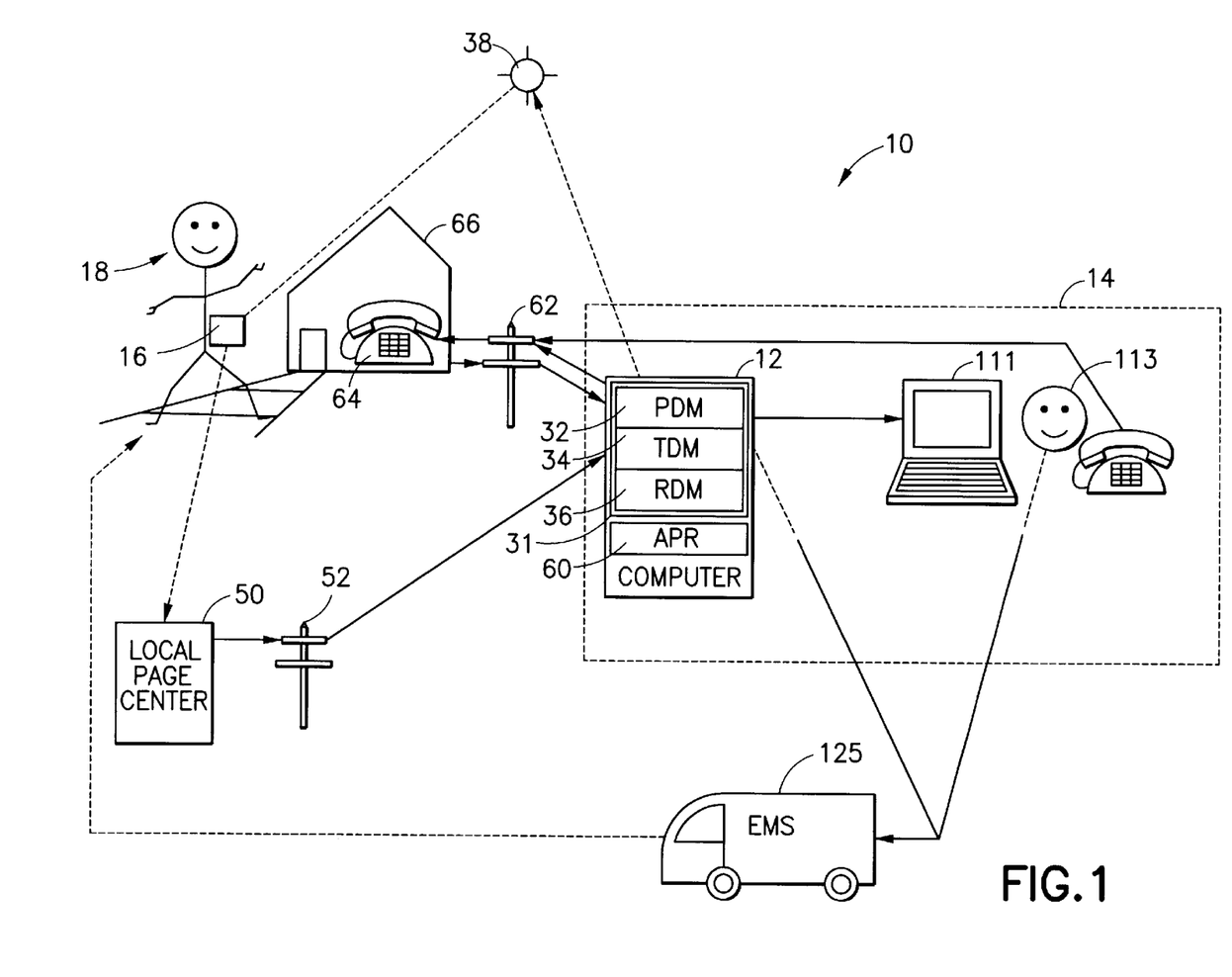
FIG. 1 is a schematic of the medical communication system for ambulatory home-care patients according to the invention.

Turning now to FIG. 1, an overview of an out-patient medical communication system 10 is shown. Generally, the system 10 includes a health care provider computer 12 housed at a health care provider facility 14 (or in a third party facility) and a two-way paging device 16 worn by a patient 18. As described in more detail below, the computer 12 is arranged to be in two-way communication with the pager 16.

Figure 2:
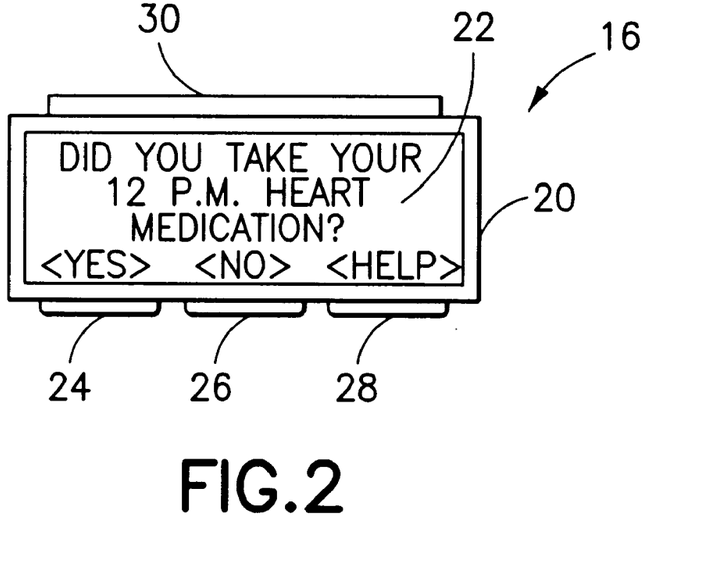
FIG. 2 is a top view of a two-way pager used in the medical communication system for ambulatory home-care patients according to the invention.
Figure 3:
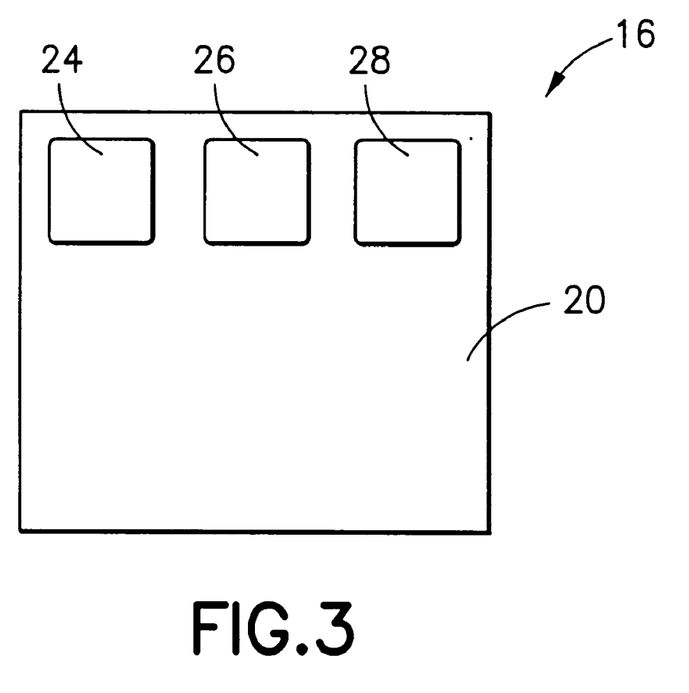
FIG. 3 is a side elevation view of the two-way pager shown in FIG. 2.

Referring to FIGS. 2 and 3, the paging device 16 includes a housing 20 having an alphanumeric display 22, a plurality of buttons 24, 26 for responding to received messages, a signal emitter (e.g., a sound generator or vibration generator) (not shown), and preferably also includes a belt clip 30. The pager may also include a 'help' or so-called panic button 28 for requesting immediate assistance.

The computer 12 includes a memory or memories 31 which includes a patient data module (PDM) 32, a treatment data module (TDM) 34, and a report data module (RDM) 36, at least the PDM and TDM modules preferably being stored as software data arrays. The PDM 32 stores vital statistics on patients. For example, vital statistics for a given patient may include the patient's name, pager number, home phone number, home address, medical condition, age, health care provider, emergency contact phone numbers (e.g., relatives and neighbors), emergency medical services local to the home of the patient, and all other pertinent data related to that patient. The TDM 34 stores patient treatment plans, particularly including pharmacological administration schedules (what medicines to self-administer and when), inquiry scripts (questions posed to the patient based upon the pharmacological administration schedules), and patient contact schedules (when to engage the patient with an inquiry script). The inquiry scripts are sent, typically via satellite 38 as shown in FIG. 1 (or via mountaintop transmitter, or micro- or macro-cellular systems), to the two-way pager 16 provided to the patient 18. For example, the script may include the following series of questions, available responses, and comments:

Did you take your 12:00 pm heart medication? (Yes) (No)

Did you experience any unusual side effects? (Yes) (No)

Would you like a health care provider to contact you? (Yes) (No)

Will you be available to respond to your 4:00 pm medication inquiry? (Yes) (No)

This inquiry is concluded. Should you have any questions, please call 800-555-1234. The RDM 36 records and stores detailed information regarding communications between patients and the computer and may be implemented as an analog (e.g. tape) recorder or a digital (e.g. disk memory) recorder. The detailed information may include, for example, the time and date of a communication and the patient response to a script. The RDM 36 serves as a quality assurance record for the health care provider and may also serve as an empirical medical and legal "document" which verifies the compliance by the patient with the treatment. In addition, the computer 12 uses information stored in the RDM to provide reporting functions (e.g., statistical analysis and charting) regarding the communications between the patients and the computer. For example, the computer 12 may provide the "dropout ratio"; i.e., the predictability of receiving a response from particular patients. The "dropout ratio" is a measure of the effectiveness of the technology for a particular patient and may be used to determine when a particular patient needs to be removed from the technology of the invention and cared for through more conventional means. The reporting functions may also be used to adjust the time period for the "timeout", defined and described hereinafter.

The computer 12 determines which patients are to be contacted, and when they are to be contacted, based upon patient data stored in the PDM 32, and associated patient contact schedules stored in the TDM 34 and a clock (not shown) of the computer. The computer 12 initiates a communication with a patient by placing a call to a patient's pager using commercially available telecommunication hardware and software and/or pager contact software implemented elsewhere on the computer.

Figures 4, 4A:
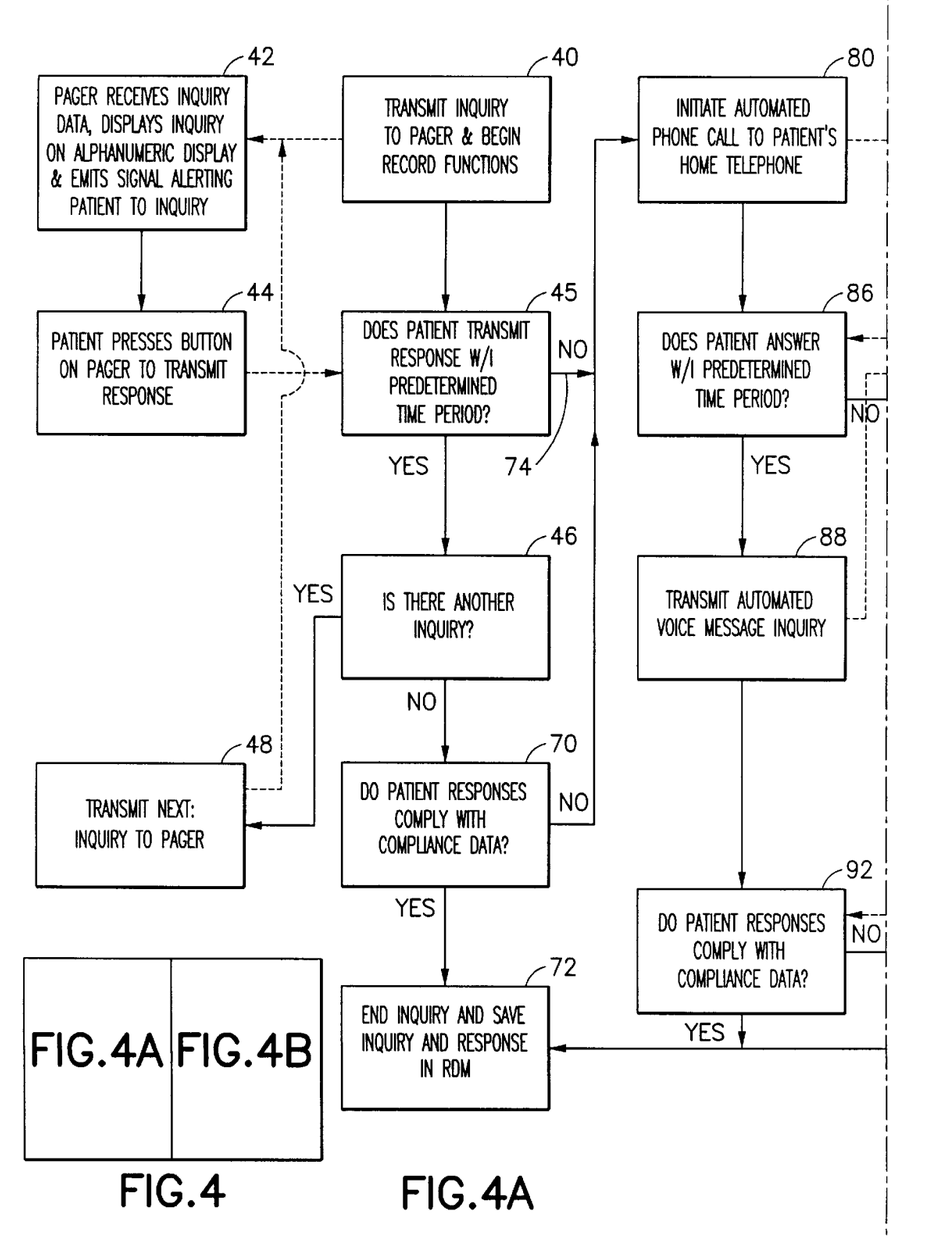
FIG. 4 (represented as FIGS. 4A an 4B on two separate sheets) is a flow diagram of the operation of the medical communication system for ambulatory home-care patients with communications between the care provider system and the patient indicated by dashed arrows and processes occurring within the care provider system indicated by solid arrows.
Figure 4B:
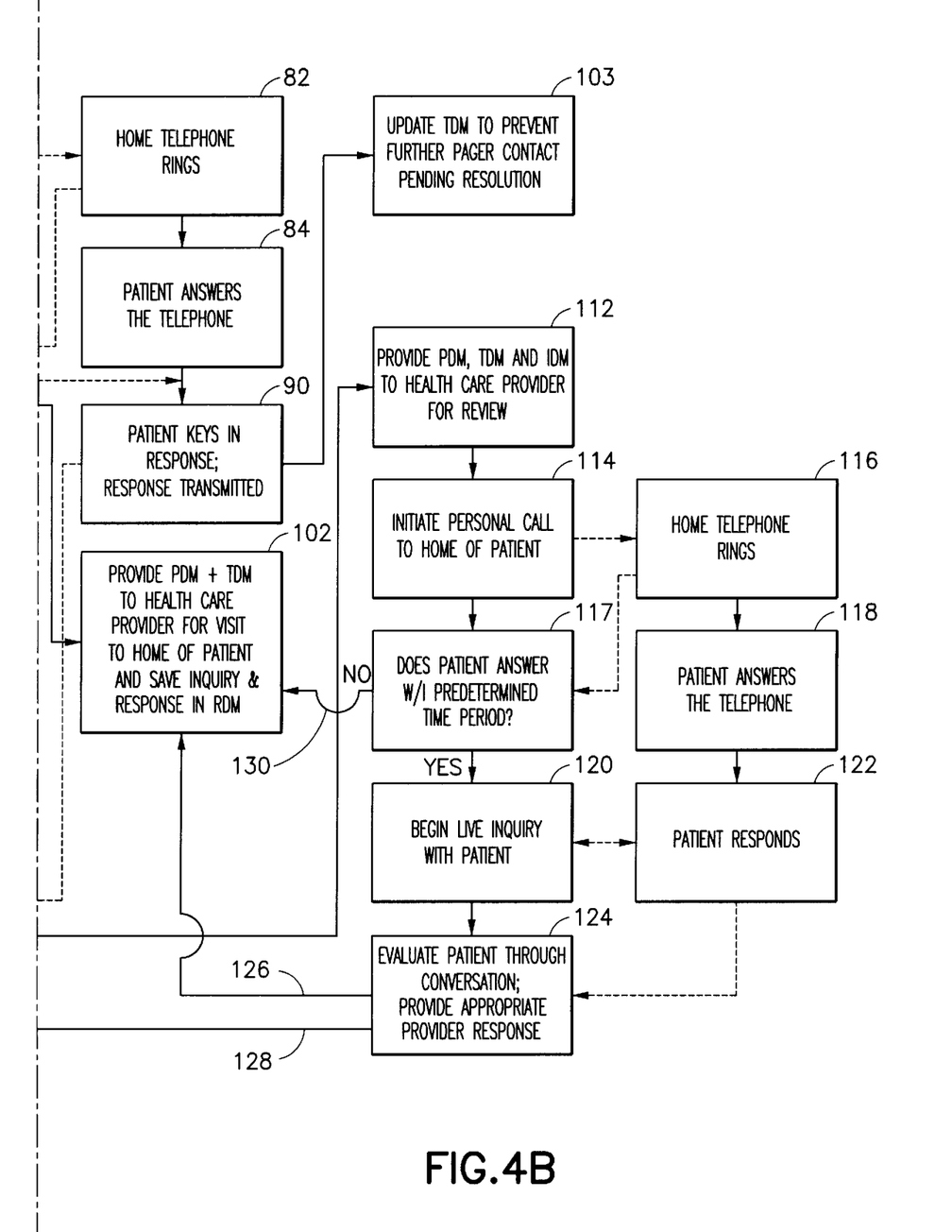

Referring now to FIGS. 1 and 4, at 40, upon placing the call to the pager 16, a first question (or inquiry) from a script which is stored in the TDM 34 is transmitted to the two-way pager 16 provided to the patient 18, and the RDM 36 associated with the patient is activated. Upon receipt 42 of the first pager inquiry, the pager emits a signal to inform the patient that an inquiry is being received. If the patient is available to respond; i.e., the patient is wearing the pager or otherwise near the pager and is coherent to adequately respond, the question is answered (or responded to) by the patient's activation of a response mechanism (for example, by pressing one of the buttons 24 and 26 in FIGS. 2 and 3) on the pager to transmit 44 a 'Yes' or 'No' response to the question posed. The pager transmits the response, preferably over local lines to a local paging center 50 which forwards the answer over land lines 52 or satellite, to the computer 12 at the health care provider facility 14 where the answer is recorded in the RDM 36. At 45, the computer determines whether the patient has responded within a given time frame ("timeout"). If not, the computer will proceed at 74, as described hereinafter. If the patient does respond before the timeout, the timeout is reset and subsequent questions 46 of inquiry are transmitted 48 by the computer and the pager receives 42 and displays the questions. An alerting signal, although not required for each inquiry of a session, may be provided before each question. The patient replies at 44 to each question in turn prior to a timeout; otherwise the computer will proceed at 74. The operation of two-way transmission and receipt of messages by paging, for example, as provided by the SkyTel 2-Way$^{SM}$ service offered by SkyTel, is known by those skilled in the art.

Each response received back at the computer 12 is compared at 70 with complying answers stored in the TDM to indicate whether the patient is following his/her prescribed course of treatment and whether the patient believes that further health care provider contact is not required until the next inquiry. If all the answers are in compliance, the present inquiry is ended at 72 and the RDM stops recording and stores the communication between the computer and the patient.

If the patient fails to respond to the initial pager inquiry within a given time frame ("timeout") at 45 (for example, one minute) or provides at 70 at least one response which is not in compliance with answers stored in the TDM (for example, the patient responds that he has not self-administered required medication or that he is experiencing unusual side effects), an automated phone call routine (APR) 60 is initiated at 80 by the computer 12. The APR 60 is preferably provided as software in the computer 12. The APR 60 preferably operates via land-line telephonic communications 62 to call a touch-tone telephone 64 located at the home 66 of the patient 12. The APR 60 functions to provide a back-up for a patient who is at home but not in the vicinity of his/her beeper, or who may have inadvertently provided a non-complying response. The APR 60 places a call (via the telecommunications hardware and software) to a telephone at the home of the patient, causing a ring 82 (or other signal) to alert the patient. If the patient answers the telephone at 84 within a predetermined time period (or number of rings) as determined at 86, the automated phone call routine at 88 transmits to the patient pre-recorded or electronic voice message questions; preferably the same TDM inquiries initially sent to the pager of the patient. The patient is preferably cued to respond to each question by pressing keys on the telephone which designate 'Yes' or 'No' responses. In the alternative, or in addition, responses may be spoken into the telephone receiver and "translated", using voice recognition software stored at the computer. The responses are sent at 90, preferably via land-line, back to the computer 12 and compared at 92 with complying answers stored in the TDM. Preferably, a final comment is sent to the patient reminding the patient to wear and respond to the pager. As previously mentioned, all questions and responses are recorded (at 42) and stored by the RDM. If the responses now indicate 76 that the patient is following his/her prescribed course of treatment and believes himself/herself to not require further care, the present inquiry is ended 72.

If, at 86, the patient fails to answer the touch-tone telephone within a predetermined number of rings, e.g., six rings of the telephone, or if an answering machine answers the phone, at 102 the computer preferably displays the patient's PDM, TDM, and RDM data on a display screen 111 monitored by trained personnel 113; e.g., a staff nurse, and updates at 103 the patient's TDM to prevent further scheduled pager contact pending a satisfactory resolution regarding the patient's whereabouts and condition. The nurse reviews the patient's data, including telephone numbers for relatives, neighbors, and emergency medical services personnel local to the home of the patient, and instructions stored in the PDM for a recommended cause of action based on failure to contact the patient. For example, the recommended cause of action for a particular patient may instruct the nurse to send emergency medical services personnel to the home of the patient to investigate; while for another patient, emergency action may only be taken if the failure to contact the patient continues over a period of time.

If the patient answered the telephone but provided at 92 noncomplying answers, the computer displays the patient's PDM, TDM, and RDM data on the display screen 111 monitored at 112 by the staff nurse 113. The nurse reviews the patient's PDM, TDM, and RDM data to briefly assess the exigency of the circumstance and initiates at 114 a phone call to the patient's home telephone to speak with the patient, causing a telephone at the home of the patient to ring at 116. If, before a timeout 117, the patient answers the telephone at 118, based upon the conversation 120, 122 between the nurse and the patient, and the patient's PDM, TDM, and RDM data, the nurse may respond at 124 by sending emergency medical personnel 125 to the home of the patient as indicated at 102, by scheduling at 102 a non-emergency visit between the patient and a health care provider, or by concluding that the patient does not need further assistance, and ending the inquiry at 72. The conversation and nurse's recommended response are stored (72 or 102) in the patient's RDM. If the patient fails at 130 to answer the telephone, the nurse provides an appropriate response, e.g. contacting a neighbor to go the home of the patient or sending emergency medical personnel to the home of the patient at 102. As previously mentioned, if personal intervention is required at 102, the TDM for the patient is adjusted at 103 pending resolution of the matter so that the same situation will not be repeated hours later unnecessarily.

It will be appreciated that the medical communication system permits an ambulatory home-care patient to be contacted within and outside the home of the patient, as the system for interacting with the patient is a portable two-way pager which operates over a relatively large area. Therefore, the patient is not confined to his/her home in order to respond to a care system stationed in his/her home. In addition, a multi-level inquiry is established to determine the condition of the patient and the questions of the inquiry and the responses are stored in the computer to verify and evidence that an appropriate response by the health care provider to the responses supplied by the patient has been provided. Moreover, the paging system is relatively inexpensive, especially when compared with current telemedicine systems, and provides a level of interactivity which is reassuring to the patient.

There have been described and illustrated herein a medical communication system and a method of communicating with an ambulatory home-care patient to insure the patient's compliance with a treatment plan. While particular embodiments of the invention have been described, it is not intended that the invention be limited thereto, as it is intended that the invention be as broad in scope as the art will allow and that the specification be read likewise. Thus, while a satellite paging system has been disclosed for initiating communication with an ambulatory out-patient, it will be appreciated that other portable communication devices such as non-satellite pagers, cellular phones, personal digital assistants (PDA's), palm-held computers, and wristwatch-type pagers, may also be used to provide two-way voice or text messaging. In fact, any portable communication device can be used in a likewise manner. Also while the pager has been disclosed to include a sound and/or vibratory emitter, it will be appreciated that the pager may be designed to emit light and/or vibration for the hearing impaired. In addition, the pager may include more buttons for more particularized responses. Also, while the pager is described as having an alphanumeric display, it may, in the alternative or in addition, have an iconic display. Furthermore, the TDM may include information other than that particularly described above; for example, exercise schedules, the patient's generally perceived state of health, doctor appointments, and more may all be provided. The inquiry scripts may include questions beyond the patient's compliance with scheduled pharmacological administration, including reminders of scheduled appointments with doctors, compliance with dietary restrictions, compliance with exercise regimens, and whether the patient will be available to answer the next scheduled inquiry (i.e., certain patients can be given the option to defer a later scheduled contact). Moreover, while it is preferable to pass the PDM, TDM, and RDM data of a patient supplying non-complying answers to a staff nurse for review, it will be appreciated that the computer can be configured to automatically place a call directing emergency staff to the home of the patient without prior staff review. Also, while the system has been described to direct an automatic phone call with voice messages to a patient supplying non-compliant responses or failing to supply any response, it will be appreciated that the system may direct a live staff-operated call to the home of a patient immediately after receipt of non-compliant responses or after failure to receive any response prior to "timeout". In addition, while the PDM, TDM, and RDM have been described as separate modules, it will be appreciated that the PDM, TDM, and RDM may be combined into a single module or may be otherwise grouped. It will therefore be appreciated by those skilled in the art that yet other modifications could be made to the provided invention without deviating from its spirit and scope as so claimed.

We claim:

1. A portable home-care patient communication system for use by a patient, comprising:
   a) a computer system having a memory means, a first transmitting means, and a first receiving means, said memory means storing a personal data module and treatment module for the patient, said treatment module including a treatment plan, first and second inquiry data, and compliance data; and
   b) a portable communication device having a display, second receiving means for receiving first inquiry data, and second transmitting means for transmitting a first response and a second response, said communication device adapted to be carried by the patient within and outside the home of the patient,
   wherein said first transmitting means is for transmitting in sequence said first and second inquiry data from said computer system to said second receiving means of said portable communication device,
   said first receiving means is for receiving at said computer system said first and second responses transmitted by said second transmitting means of said portable communication device, and
   said first and second responses are compared with said compliance data by said computer system to determine whether the patient is complying with said treatment plan.

2. A portable home-care patient communication system according to claim 1, wherein:
   said portable communication device is adapted to be wearable by the patient.

3. A portable home-care patient communication system according to claim 1, wherein:
   said portable communication device has an alphanumeric display.

4. A portable home-care patient communication system according to claim 1, wherein:
   said portable communication device is a two-way pager.

5. A portable home-care patient communication system according to claim 1, wherein:
   said treatment plan includes a schedule of pharmaceutical self-administration.

6. A portable home-care patient communication system according to claim 1, wherein:
   said personal data module includes the name, address, portable communication device number, and home telephone number of the patient.

7. A portable home-care patient communication system according to claim 1, wherein:
   said computer system further includes a recording means for recording said first response transmitted by the second transmitting means to said first receiving means.

8. A portable home-care patient communication system according to claim 1, wherein:
   said computer system further includes a reporting means for determining an effectiveness of said patient communication system with respect to the patient.

9. A portable home-care patient communication system according to claim 1, further comprising:
   c) display means coupled to said computer system for displaying indications of said treatment plan.

10. A portable home-care patient communication system for use by a patient, comprising:
    a) a computer system having a memory means, a first transmitting means, and a first receiving means, said memory means storing a personal data module and treatment module for the patient, said treatment module including a treatment plan, first inquiry data, and compliance data;
    b) a portable communication device having a display, second receiving means for receiving first inquiry data, and second transmitting means for transmitting a first response, said communication device adapted to be carried by the patient within and outside the home of the patient; and
    c) an automated telephone means activated by said computer system for automatically calling a home telephone device at a home of the patient,
    wherein said first transmitting means is for transmitting said first inquiry data from said computer system to said second receiving means of said portable communication device,
    said first receiving means is for receiving at said computer system said first response transmitted by said second transmitting means of said portable communication device,
    said first response is compared with said compliance data by said computer system to determine whether the patient is complying with said treatment plan, and
    wherein said automated telephone means transmits at least one voice message to the home telephone device.

11. A portable home-care patient communication system according to claim 10, wherein:
    said computer system further includes a recording means for recording a response to said at least one voice message.

12. A portable home-care patient communication system according to claim 10, further comprising:
    timeout means for causing said automated telephone means to automatically call the home telephone device when said first receiving means fails to receive said first response from said second transmitting means within a predetermined period of time after said first transmitting means transmits said first inquiry data to said second receiving means.

13. A portable home-care patient communication system according to claim 10, wherein:
    said automated telephone means automatically calls the home telephone device when said first response, when compared with said compliance data, indicates that the patient is not complying with said treatment plan.

14. A portable home-care patient communication system according to claim 10, further comprising:
   d) display means coupled to said computer system for displaying indications of said treatment plan.

15. A method of communicating with an ambulatory home-care patient, comprising:
   a) providing a portable communications device to a patient;
   b) automatically transmitting a multi-level inquiry from a computer to the portable communications device;
   c) in response to the patient activating a response mechanism on the portable communication device to transmit a plurality of responses to the multi-level inquiry, receiving at the computer the plurality of responses from the portable communications device; and
   d) comparing the plurality of responses to compliance data stored in the computer.

16. A method of communicating with an ambulatory home-care patient according to claim 15, wherein:
   the plurality of responses transmitted from the computer to the portable communications device via one of satellite or land-based telephone lines.

17. A method of communicating with an ambulatory home-care patient according to claim 15, further comprising: e) recording the plurality of responses in a memory storage means.

18. A method of communicating with an ambulatory home-care patient, comprising:
   a) providing a portable communications device to a patient;
   b) automatically transmitting an inquiry from a computer to the portable communications device;
   c) in response to the patient activating a response mechanism on the portable communication device to transmit a first response to the inquiry, receiving at the computer the first response from the portable communications device;
   d) comparing the first response to compliance data stored in the computer; and
   e) statistically analyzing the frequency of receiving at the computer a first response relative to transmitting an inquiry from the computer.

19. A method of communicating with an ambulatory home-care patients, comprising:
   a) providing a portable communications device to a patient;
   b) automatically transmitting an inquiry from a computer to the portable communications device;
   c) in response to the patient activating a response mechanism on the portable communication device to transmit a first response to the inquiry, receiving at the computer the first response from the portable communications device;
   d) upon receiving the first response, comparing the first response to compliance data stored in the computer;
   e) upon failure to receive at the computer a first response from the portable communications device or upon receiving a first response at the computer which is non-complying with the compliance data stored in the computer, contacting a telephone device at a home of the patient using an automated dialing system;
   f) sending a voice message from the computer to the telephone device;
   g) in response to the voice message, receiving at the computer from the telephone device a second response; and
   h) comparing the second response to compliance data stored in the computer.

20. A method of communicating with an ambulatory home-care patient according to claim 19, further comprising:
   i) recording the second response in a memory storage means for storing said second response.

21. A method of communicating with an ambulatory home-care patient according to claim 20, further comprising:
   j) recording the first inquiry and the second inquiry in a memory storage means for storing said first and second inquiry.

* * * * *

UNITED STATES PATENT AND TRADEMARK OFFICE
CERTIFICATE OF CORRECTION

PATENT NO.   : 5,902,234
DATED        : May 11, 1999
INVENTOR(S)  : Nicholas J. Webb Page 1 of 1

It is certified that error appears in the above-identified patent and that said Letters Patent is hereby corrected as shown below:

<u>Column 3,</u>
Line 63, "The RDM 36 records…" should be a new paragraph.

<u>Column 9,</u>
Line 13, delete "communication" and insert -- communications --, therefor.
Line 36, delete "communication" and insert -- communications --, therefor.

<u>Column 10,</u>
Line 10, delete "communication" and insert -- communications --, therefor.

Signed and Sealed this

Sixteenth Day of July, 2002

*Attest:*

*Attesting Officer*

JAMES E. ROGAN
*Director of the United States Patent and Trademark Office*